United States Patent
McDermott et al.

(10) Patent No.: US 9,662,189 B2
(45) Date of Patent: May 30, 2017

(54) STRESS-REDUCED DENTURE BASE DISC

(71) Applicant: CMP INDUSTRIES LLC, Albany, NY (US)

(72) Inventors: Richard McDermott, Ballston Spa, NY (US); Devon O. Howe, Saratoga Springs, NY (US)

(73) Assignee: CMP Industries LLC, Albany, NY (US)

( * ) Notice: Subject to any disclaimer, the term of this patent is extended or adjusted under 35 U.S.C. 154(b) by 445 days.

(21) Appl. No.: 14/210,482

(22) Filed: Mar. 14, 2014

(65) Prior Publication Data

US 2014/0272798 A1    Sep. 18, 2014

Related U.S. Application Data

(60) Provisional application No. 61/782,888, filed on Mar. 14, 2013.

(51) Int. Cl.
*A61C 13/20* (2006.01)
*A61C 13/01* (2006.01)
*A61C 13/00* (2006.01)

(52) U.S. Cl.
CPC .............. *A61C 13/04* (2013.01); *A61C 13/20* (2013.01); *A61C 13/0004* (2013.01)

(58) Field of Classification Search
CPC ... C04B 35/14; C04B 35/488; C04B 35/5805; C04B 35/117; C04B 35/185; C04B 35/481; C04B 35/653; C04B 35/52; F01D 5/20
USPC ....... 264/16, 17, 19, 20, 113, 320, 324, 294, 264/299; 425/110, 112, 117, 352, 353, 425/355, 394
See application file for complete search history.

(56) References Cited

U.S. PATENT DOCUMENTS

| | | | | |
|---|---|---|---|---|
| 1,803,814 A * | 5/1931 | Spengler | ............... | B30B 11/005 264/113 |
| 4,968,468 A * | 11/1990 | Leinweber | ............... | B30B 11/34 100/226 |
| 5,073,099 A * | 12/1991 | Kayano | ................... | B29C 43/18 100/193 |
| 5,151,044 A | 9/1992 | Rotsaert | | |
| 5,830,305 A * | 11/1998 | Andersen | ............ | B28B 23/0087 156/242 |
| 6,767,505 B2 * | 7/2004 | Witherspoon | .......... | B22F 3/087 419/45 |
| 6,808,662 B1 * | 10/2004 | Hogenkamp | ......... | B29C 43/006 264/325 |
| 7,943,068 B2 | 5/2011 | Panzera | | |
| 8,641,938 B2 | 2/2014 | Howe | | |
| 2005/0023710 A1 * | 2/2005 | Brodkin | ............. | A61C 13/0003 264/16 |

(Continued)

*Primary Examiner* — Nahida Sultana
(74) *Attorney, Agent, or Firm* — John M. Hammond; Patent Innovations LLC

(57) ABSTRACT

A method and apparatus for making a denture base disc that is used subsequently to form a removable denture. A vessel with an elastomeric lining is used to form the denture base disc so that the compression of the elastomeric material is approximately equivalent to the shrinkage of the denture base disc material during its polymerization. The vessel and elastomeric lining contained therein work cooperatively to cause the denture base disc to cure in a homogenous manner with consistent pressure on all sides so that residual stresses in the finished disc are minimized.

18 Claims, 14 Drawing Sheets

(56) References Cited

U.S. PATENT DOCUMENTS

| | | | |
|---|---|---|---|
| 2013/0295304 A1* | 11/2013 | Moore | F16D 65/10 428/34.6 |
| 2013/0313738 A1* | 11/2013 | Carden | A61C 13/0006 264/16 |
| 2016/0230007 A1* | 8/2016 | Johnson | C08L 91/06 |

* cited by examiner

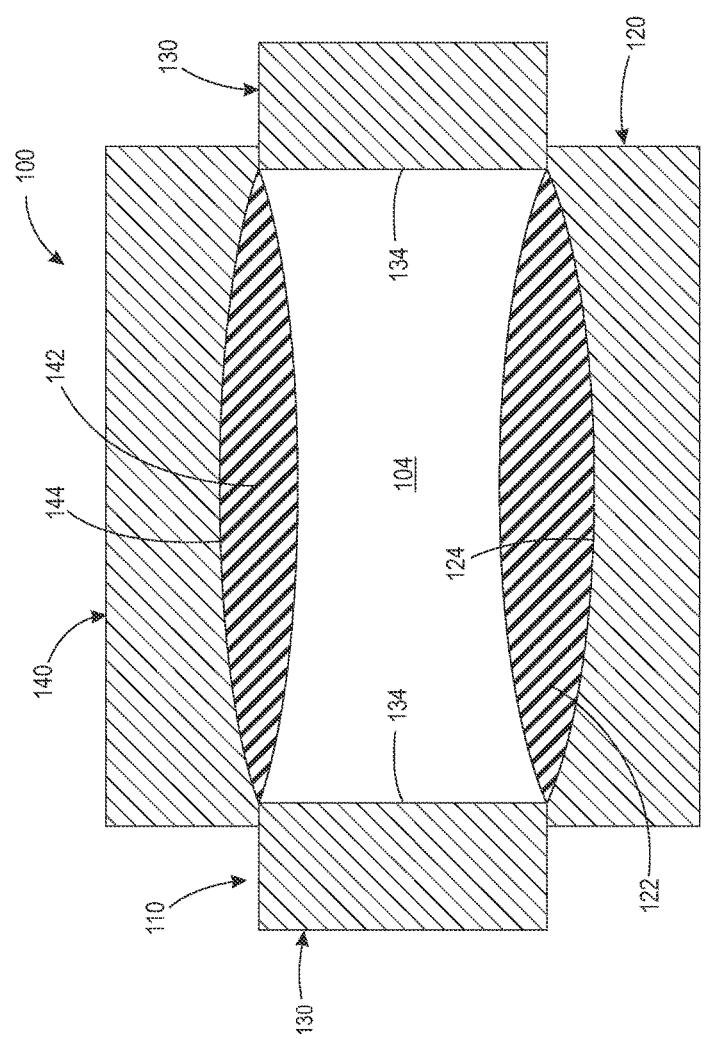

STRESS-REDUCED DENTURE BASE DISC

CROSS-REFERENCE TO RELATED PATENT APPLICATIONS

This application claims priority from U.S. provisional patent Application No. 61/782,888 filed Mar. 14, 2013, the disclosure of which is incorporated herein by reference.

BACKGROUND

Technical Field

Dental prostheses and apparatus and methods of manufacturing them. In particular, a method and apparatus for making a denture base disc as a starting material for a denture. The denture base disc has significantly reduced stresses and other defects and can be used advantageously in computer-implemented (CAD-CAM) methods to form a removable denture.

Description of Related Art

According to current practice, conventional dentures are made by a dental laboratory using a "lost wax" technique. In this technique, a denture base is formed out of wax on a baseplate fitted to a stone model; then plastic denture teeth are fitted into the wax. More wax is added to form interproximal (between the teeth) contours and to make the denture appear life-like. This waxed denture (known in the industry as a "wax-up") is then delivered to a dentist for fitting into the patient's mouth. At that time, the dentist evaluates the aesthetics of the teeth of gums, and function of chewing and speech by the patient.

If adjustments are required to the wax-up, the dentist may make adjustments to the wax and/or position of the teeth, or the dentist may give instructions to the laboratory to make such adjustments. After the adjustments are made and the dentist is satisfied with the wax-up, the dental laboratory converts the wax and baseplate into a rigid methylmethacrylate plastic through a "lost wax" processing technique. This process involves the following steps:

1) A liquid slurry of a gypsum-based powder known as "dental stone" or plaster is poured into the bottom half of a metal denture flask.
2) Before the liquid dental stone begins to harden to form a solid, the lower region of the wax-up model is pushed into the liquid stone so that the liquid stone rises to the upper edge of the flask bottom half. The wax up model, which consists of the baseplate and wax denture base and the plastic denture teeth embedded in the wax base, is only immersed into the liquid stone a small distance, such that the liquid stone does not cover the teeth of the wax-up. Excess stone is removed from overflow areas on the flat edge of the flask where it will interface with an opposing flask half before the stone hardens to make it smooth and relatively flat so that no undercuts are created.
3) When the liquid dental stone hardens, its exposed top surface is coated with a separating medium such as petroleum jelly (or foil).
4) The top half of the denture flask is placed on top of the bottom half, and thus extends upwardly above the wax-up. Additional liquid dental stone slurry is poured into the top half of the flask to cover the top portion of the wax-up, including the teeth that are embedded in the wax.
5) After the dental stone has fully hardened, the flask and wax-up that is contained therein are heated to soften the wax.
6) The flask is opened, i.e., the top half and bottom half of the flask are separated. The top half of the dental flask now contains the plastic denture teeth embedded in the solid dental stone. The melted wax is washed-out with boiling water and any remaining wax is removed from the dental stone and plastic denture teeth with a brush, boiling water and soap. Sometimes, a chemical wax remover is used, followed by soap and water. Any trace of remaining wax may cause a failure of the bond between the denture teeth and the denture base. This problem is frequently the cause of denture teeth dislodging from the denture base during function (patient chewing).
7) Since the plastic denture teeth are embedded into the solid dental stone which is contained in the top half of the flask, care must be maintained not to dislodge the teeth from the stone. In order to enhance the bond between the plastic teeth and the denture base that will subsequently be formed and bonded to them, a dental laboratory technician will sometimes lightly grind the exposed surfaces of the teeth that were embedded in the wax in order to break the shiny surface (glaze) on the surfaces. In some cases, a technician will also drill very small holes into the exposed teeth bottoms (sometimes called "diatorics") in order to allow denture base material to flow into the holes, thereby improving mechanical retention. However, the use of diatorics is risky because they often are the cause of denture tooth fracture.
8) The denture base material is then prepared and contacted with the teeth to form the denture. The most common type of denture base material used in the United States is a heat-cured methylmethacrylate material. Methylmethacrylate powder and a suitable liquid are mixed together to form a dough. The dough is placed in the void volumes of the top half of the flask which contain the artificial teeth. The void volume in the top half of the flask previously contained a portion of the wax, which was removed as described above; this top void volume now forms a mold of the upper portion of the denture base, into which the bottoms of the teeth embedded in the dental stone extend. In like manner, the void volume in the bottom half of the flask also previously contained a portion of the wax, which was removed as described above; this bottom void volume now forms a mold of the lower portion of the denture base. After placing a thin sheet of polyethylene on the bottom half, the top and bottom halves of the flask are placed together, forming a complete mold of the denture base with the dough contained therein. The flask is then placed in a press at approximately 1,000 psi to compress the dough, thereby squeezing the dough and causing it to flow into the voids that were once wax.
9) Because methylmethacrylate polymers shrink when they polymerize, it is common practice to "trial pack" the denture several times. "Trial packing" means that the denture base dough is placed in the flask and pressed, then the flask is opened again and more dough is added, then closed and pressed again. This process is repeated until the operator subjectively determines that the denture base is packed as tightly as possible. Before the last packing is done, the thin polyethylene sheet is removed from the bottom half. The last "trial pack" is typically performed at about 3,000 psi.
10) The flask then is inserted into hot water to start the polymerization process. Most heat-cured methylmethacrylate polymers are cured at about 165° F. for a few hours; then the water temperature is increased to boiling (approximately 212° F.) for at least 30 minutes. The purpose of the lower temperature cycle is to initiate polymerization. If the temperature is initially too hot, the polymer will cure too quickly, causing porosity in the denture base. The porosity is caused by rapid curing and shrinkage of the polymer before uncured polymer can fill the shrinking area. The purpose of raising the temperature at the end of the cycle is to complete the polymerization process as much as possible.

11) The last steps are to remove the denture from the flask by opening the two flask halves; then use plaster nippers or an air chisel to remove stone from the denture (devesting); then the denture base is adjusted with a high-speed bur and polished with a rag wheel and abrasives and/or polishing media.

There are many problems with this conventional denture base fabrication method and related materials and systems:

1) Due to the many steps of processing a denture as summarized above, there are chances of introducing an error into the steps, thereby potentially increasing fit problems.
2) Tooth de-bonding from the denture base is a common problem. This is often caused by the presence of traces of remaining wax on the bottoms of the teeth, which cause a failure of the bond between the denture teeth and the denture base. Tooth fracture is also a common problem, particularly when diatorics are used in an attempt to strengthen the bond of the teeth to the denture base as described above.
3) Human errors cause inconsistencies in the denture fabrication process, which can result in defects and failures as described above, and/or poor denture fit. Examples of human errors are using different ratios of methylmethacrylate powder/liquid, using different flask closure pressures, water levels, or temperatures that vary from fabrication to fabrication. Inconsistencies can also be caused by environmental variation, such as differences in ambient temperature and/or humidity. Underpacking is an error caused by not using enough dough or too little clamping pressure. This can result in porosity (small bubbles) that may weaken the denture and make it prone to bacteria growth. Overpacking occurs when too much dough is used and then the flask halves don't fully close together and have intimate contact. This can result in mal-fitting dentures or "open bites" as is referred to by dentists. Another introduction of potential for human error is the finishing step. In the process of removing imperfections in a denture that has been devested, some dental technicians may over adjust (remove excessive denture base material), resulting in denture base that is too thin and prone to breakage. Also, the polishing step—which is the process to remove scratches created in the finishing step—a dental technician may over-polish the denture teeth, which can remove intended delicate imperfections in the artificial teeth or anatomy that may alter the esthetics and/or function of the artificial teeth.
4) Denture base material shrinkage causes internal stresses which are a source of denture fit problems. During the denture base forming part of the process, methylmethacrylate denture base material polymerizes and shrinks rapidly at first, causing internal stress in the denture base, especially in areas of differing thicknesses. After a denture in devested (removed from denture flask), this internal stress may cause dimensional distortion. Although some commercial continuous pressure curing systems (such as the Ivocap® system by Ivoclar Vivodent, Inc., or the Success® Injection System by Dentsply Prosthetics) reduce this stress, methylmethacrylate continues to slowly polymerize over time until residual monomers are virtually eliminated. Thus distortion (resulting in poor fit) can occur after a denture is completed by a dental laboratory and shipped to a dentist.

This last problem is illustrated in FIG. 13, which shows a cross-section of a denture base 10 taken along the midline thereof. It can be seen that the denture base 10 has regions of different thickness which may result in areas of more shrinkage than other areas during polymerization of the methylmethacrylate. For example, the thicker region 12 may undergo a greater degree of shrinkage (as indicated by large arrows 13), that the shrinkage of the thinner region 14 (as indicated by smaller arrows 15. These areas of shrinkage differential create stress points, such as stress point 16. Such stress points may cause dimensional distortion of the denture base, resulting in the denture having a poor fit to the patient's mucosa.

The dental laboratory industry in the United States is currently undergoing some changes away from "lost-wax" techniques to computer-aided-design (CAD) and computer-aided-manufacturing (CAM) of dental products. Dental crowns and bridges have been milled using CAD-CAM technologies for many years. The use of these technologies for crowns and bridges has been increasing rapidly in recent years. However, there has been very little use of CAD-CAM technologies in the area of removable prosthodontics (e.g., dentures, partials, etc.).

There are several reasons why CAD-CAM has not been more widely used in removable prosthodontics. A major reason is that satisfactory software for occlusion (i.e., mapping of how upper and lower teeth work together) has not been developed. Another reason is because a denture is made from two colors of materials (a pink base and white teeth), and dental milling systems are based on monolithic materials. Additional reasons are described in the Applicant's commonly owned U.S. Pat. No. 8,641,938 of Howe for a "Denture and Method and Apparatus of Making Same," the disclosure of which is incorporated herein by reference.

What is needed is a simple, low cost method of manufacturing a denture in which the denture is accurately formed, dimensionally stable, and robust, i.e., resistant to loosening and/or loss and/or fracture of teeth. Additionally, there is a need for a method of making a denture base disc as a starting material for a denture, which is free of stresses and other defects that result in making dentures that do not meet quality requirements.

SUMMARY

In accordance with the present disclosure, methods and apparatus are provided which meet the above need for a method of making a denture based disc.

In one broad aspect of the present disclosure, a method is provided for making a denture base disc that is used in a CAD-CAM milling technique to form a removable denture. In the method, a vessel with an elastomeric lining is used to form the denture base disc so that the compression of the elastomeric material is approximately equivalent to the shrinkage of the disc material during its polymerization. The vessel and elastomeric lining contained therein work cooperatively to cause the denture base disc to cure in a homogenous manner with consistent pressure on all sides so that residual stresses in the finished disc are minimized.

In addition, during polymerization of the denture base material in the vessel, the material may be heated to facilitate polymerization. In certain embodiments, the heating of the disc may be provided from one direction, which helps to make any residual stress in the polymerized disc material uniform or consistent along any cross-section that is parallel to the heating source. In certain embodiments, the disc may be post-cured with heat over an extended period of time to remove any remaining stress and residual monomer in the finished disc.

With the denture base disc having been thusly fabricated, there are further provided methods for making a denture comprised of a base made from the denture base disc, and a plurality of teeth joined to the base. In certain embodiments, a method of making such a denture comprises forming a first cavity in the denture base disc, the first cavity having a bottom wall and a side wall and formed to correspond to the U-shaped contour of natural teeth as arranged on maxillae or on a mandible; forming a plurality of socket cavities in the denture base disc, the socket cavities extending downwardly from the bottom wall of the first cavity into the denture base disc; casting a first fluid artificial tooth material into the plurality of socket cavities and into a portion of the first cavity, thereby filling the socket cavities and forming a top fluid surface in the first cavity; applying pressure to the first fluid artificial tooth material contained in the portion of the first cavity and the socket cavities; and causing the first fluid artificial tooth material to solidify into a first solid artificial tooth material while applying pressure to the first fluid artificial tooth material. In one embodiment, to complete fabrication of the denture, a portion of the first solid artificial tooth material is removed to form the plurality of teeth, and a portion of the denture base disc is removed to form the denture base. Further details regarding this method of making a denture are as disclosed in the Applicant's commonly owned copending U.S. patent application Ser. No. 14/180, 260, titled, "Molding Artificial Teeth in Denture Base Disc," the disclosure of which is incorporated herein by reference.

In another embodiment, a method of making such a denture comprises forming a first cavity in the denture base disc, the first cavity formed to match the contour of natural teeth as arranged on maxillae or on a mandible; filling the first cavity with a first fluid synthetic tooth material and solidifying the first fluid synthetic tooth material into a first solid synthetic tooth material; removing a portion of the first solid synthetic tooth material to form the plurality of teeth; and removing a portion of the denture base disc to form the denture base. Further details regarding this method and related methods of making a denture are as disclosed in the Applicant's commonly owned U.S. Pat. No. 8,641,938, titled, "Denture and Method and Apparatus of Making Same," the disclosure of which is incorporated herein by reference.

In another aspect of the present disclosure, a method of making a denture based disc comprises filling a cavity formed within a mold vessel with an uncured denture base material. The mold cavity is bounded by a first compressible liner contiguous with a bottom wall of the vessel. A removable mold top comprising a second compressible liner on an inner surface thereof is then fitted to the top opening of the vessel, thus enclosing the uncured denture base material between the first and second compressible liners within the mold cavity. Pressure is then applied to the uncured denture base material, thereby compressing the first and second compressible liners from an uncompressed state to a compressed state. The uncured denture base material is then cured to an at least partially cured and solid state. During this curing, the at least partially cured solid state denture base material shrinks to a lesser volume than the uncured denture base material. Concurrently, the first and second compressible liners expand from a compressed state to a less compressed state. The expansion in compressible liner volume is substantially equal to the volume of shrinkage of denture base material during the at least partial curing. In certain embodiments, the mold vessel may include a third compressible liner that is contiguous with an inner surface of the side wall of the vessel.

The method may further comprise increasing the pressure to the uncured denture base material prior to curing, thereby increasing the amount of compression of the first, second, and third compressible liners in the compressed state. The method may further comprise aging the at least partially cured solid state material at a first increased temperature to produce cured denture base material. The cured denture base material may then be heated to a second increased temperature over a period of at least 0.5 hours, and maintained at the second increased temperature for at least 0.5 hours.

In another aspect of the present disclosure, there is provided an apparatus for molding a part. The apparatus may be used to make a denture base disc. The apparatus comprises a mold vessel comprising a bottom wall, a side wall, and a top opening. The apparatus includes a first compressible liner contiguous with the vessel bottom wall. The apparatus is further comprised of a removable mold top fittable to the top opening of the vessel and comprising a second compressible liner on an inner surface thereof. When the mold top is fitted to the top opening of the mold vessel, a mold cavity is formed between the first and second compressible liners and the side wall of the vessel. The volume of the mold cavity may be made variable by varying the volume of the compressible liners. The volume of the compressible liners may be varied during a molding process performed in the mold cavity. In certain embodiments, the mold vessel may include a third compressible liner that is contiguous with an inner surface of the side wall of the vessel.

The apparatus may be further comprised of means for increasing molding pressure within the mold cavity. In certain embodiments, the means for increasing pressure may be comprised of a pressure intensifier comprised of a pipe extending through a port in the mold top and having an internal bore, and a piston movable axially between an outward position to an inward position in the internal bore of the pipe. When the piston is in the outward position, an inner end of the piston and the internal bore of the pipe define a pipe cavity volume. When the piston is moved from the outward position to the inward position, the pipe cavity volume is occupied by the piston.

During the molding of a denture base disc in the molding apparatus, the pressure intensifier may be operated to apply increased pressure to the uncured denture base material contained in the mold cavity. When the piston is displaced inwardly within the pipe from the outward position to the inward position, uncured denture base material is displaced from the pipe cavity volume within the pipe into the cavity of the mold vessel, thereby increasing the pressure of the denture base material within the mold cavity.

The apparatus may include a heat source in thermal communication with the mold vessel. In certain embodiments, the heat source is provided such that the mold vessel is heated at only one location or region. The heat source may be configured to heat the bottom wall of the mold vessel.

In accordance with the present disclosure, there is also provided a denture base disc made according to the methods described herein. The denture base disc may be aged to produce cured denture base material. The cured denture base material may consist essentially of at least one of methylmethacrylate polymer or ethylmethacrylate polymer. The denture base disc may be cured with heat that is applied from one direction. The disc may be post-cured with heat.

Advantageously, the methods and apparatus as described herein solve several problems associated with the conventional denture base methods, including the following:

1) Inconsistencies of the conventional process of making a denture base are greatly reduced.
2) The problem of the debonding of teeth from denture base material made according to the present invention is almost entirely eliminated. This is because wax is never used in the instant method. The teeth are strongly chemically bonded to the denture base. In addition, the teeth may be bonded to areas of the denture base that have been prepared with a mill. In such instances, the surface is microscopically rough, which increases bonding surface area and bonding strength, and hence mechanical retention of the teeth.
3) The methods and apparatus significantly reduce the potential for human error in the process of making a denture base.
4) A denture base disc made with the instant methods and apparatus have significantly reduced internal stresses. This reduces distortion in a denture base fabricated from such a denture base disc, resulting in improved fit of the finished denture to the patient.

BRIEF DESCRIPTION OF THE DRAWINGS

The present disclosure will be provided with reference to the following drawings, in which like numerals refer to like elements, and in which:

FIG. 1 is a schematic side cross-sectional view of a first embodiment of a molding assembly comprising a mold vessel and mold top for fabricating a denture base disc in accordance with the present invention;

Figure 1A:
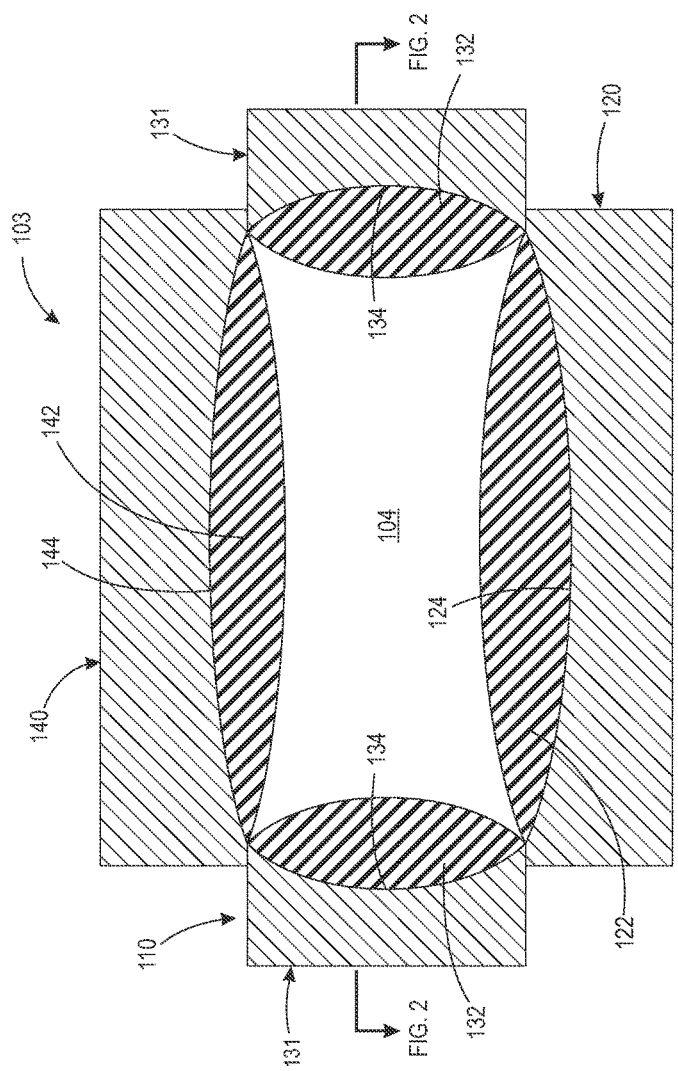
FIG. 1A is a schematic side cross-sectional view of a second embodiment of a molding assembly comprising a mold vessel and mold top.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used throughout to designate identical elements. In the following disclosure, the methods and apparatus of the present invention is described in the context of their use as a methods and apparatus for making a denture base disc. However, it is not to be construed as being limited only to use in the fabrication of denture materials. The invention is adaptable to any use in which it is desirable to make a block of polymer material that is free of internal stresses or has greatly reduced internal stresses. Additionally, the description identifies certain components with the adjectives "top," "upper," "bottom," "lower," "left," "right," etc. These adjectives are provided in the context of the orientation of the drawings, which is arbitrary. The description is not to be construed as limiting the methods and apparatus to use in a particular spatial orientation. The instant methods and apparatus may be used in orientations other than those shown and described herein.

The Applicant's methods and apparatus for making a denture base disc will now be described. It is to be understood that any denture base material compositions, vessel dimensions, vessel materials, and curing conditions such as temperatures, pressures, and times are to be considered exemplary and not limiting. The methods and apparatus may be used with parameters other than those described herein to achieve the desired results in fabricating a denture based disc.

Turning first to FIGS. 1, 1A, 2, and 3, apparatus 100 and 103 for molding a part are depicted. In the embodiments depicted therein, the part may be a denture base disc having a generally cylindrical shape, i.e., a puck shape. For other molding applications, the apparatus 100 and 103 may have an internal cavity having a different shape provided to suit the particular need.

The apparatus 100 is comprised of a mold vessel 110 comprising a bottom wall 120, a side wall 130, and a top opening 102. In certain embodiments (not shown), the bottom wall 120 and side wall 130 may be formed joined together as a single unitary piece. In the embodiment depicted in FIGS. 1-3, the bottom wall 120 and side wall 130 are provided as separate pieces and are joined together by suitable fasteners or by welding.

Figure 3:
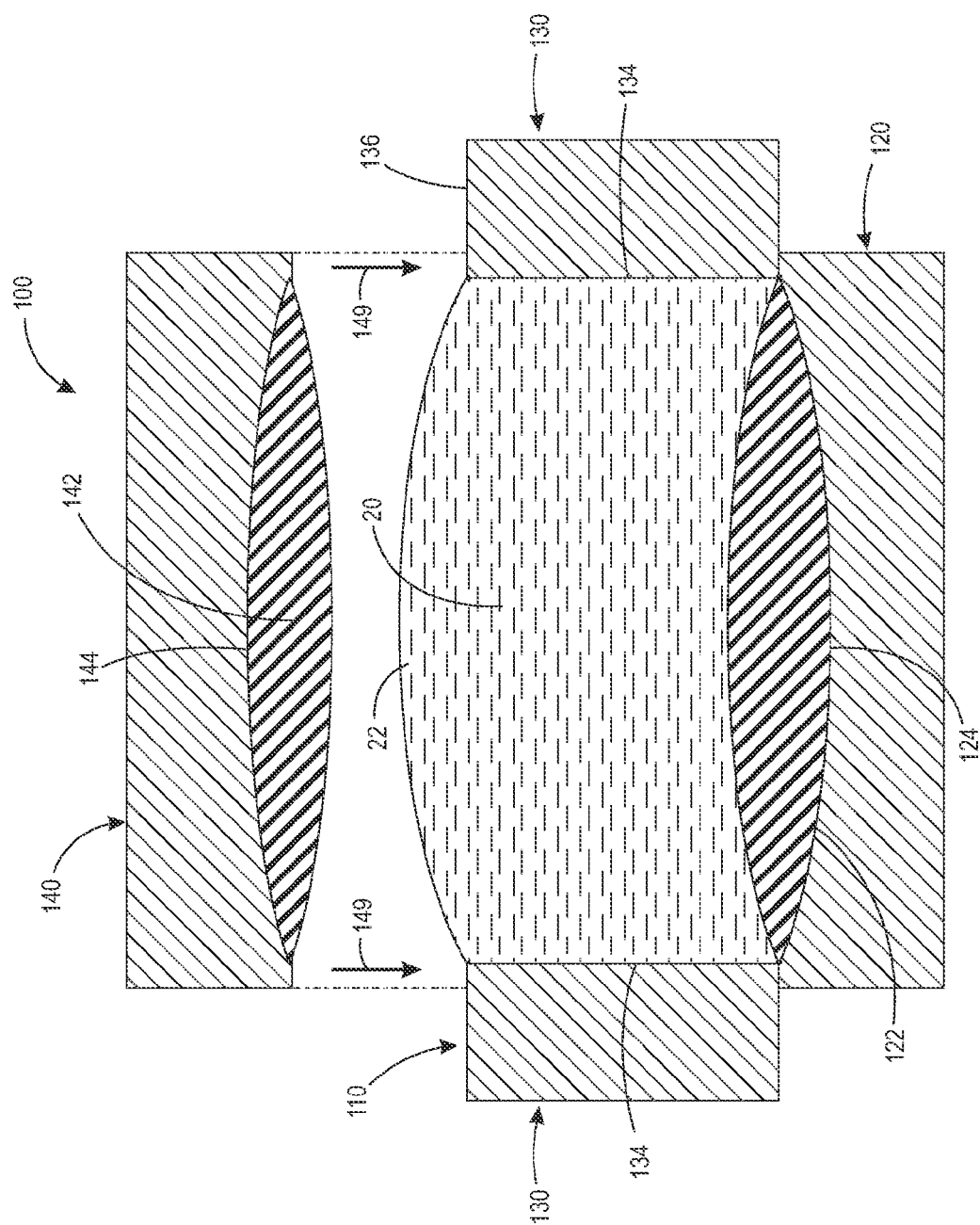
FIG. 3 is a schematic side cross-sectional view of the mold vessel and mold top as shown in FIG. 1, but with the mold top removed, and the mold cavity filled with uncured denture base material.
Figure 4:
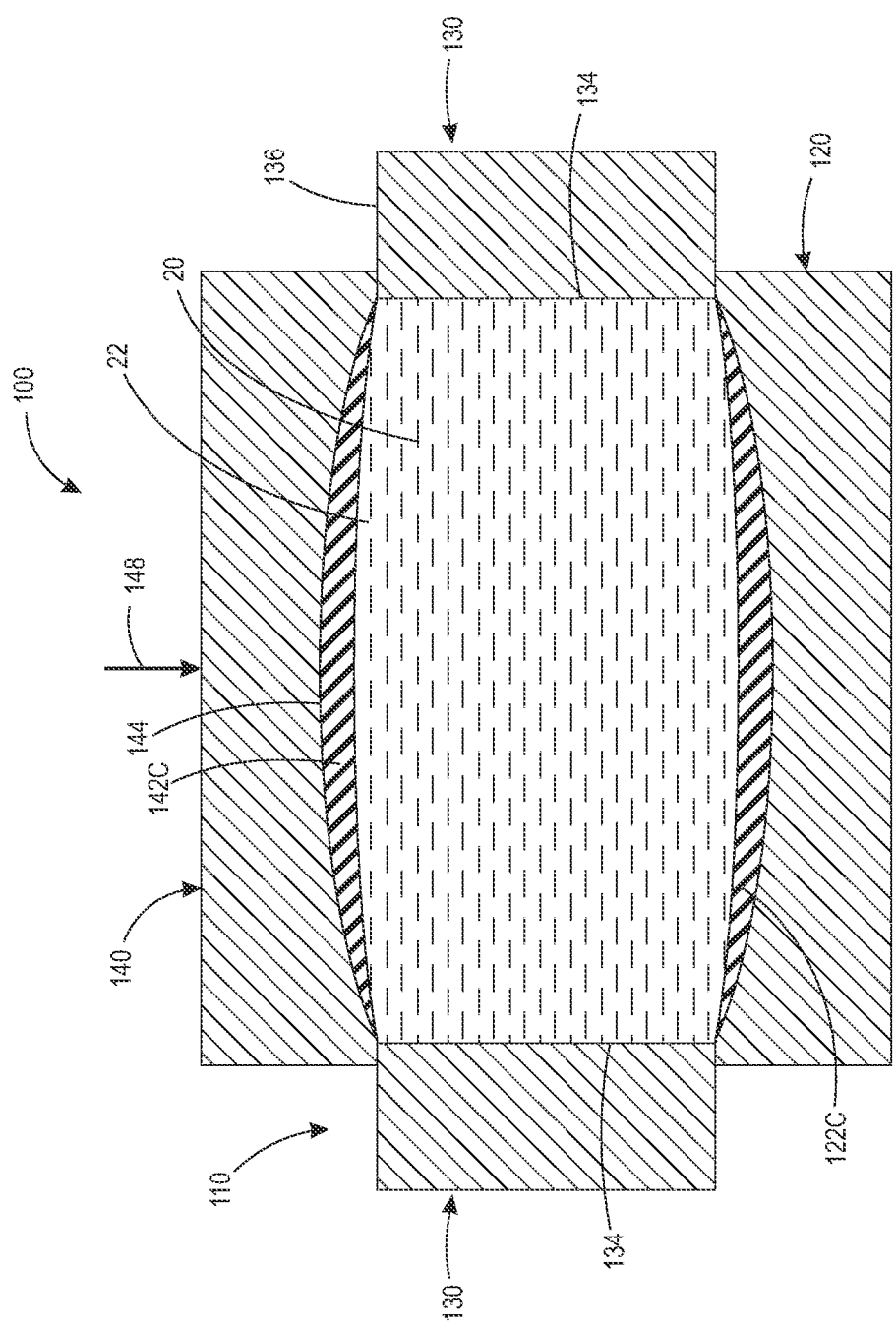
FIG. 4 is a schematic side cross-sectional view of the mold vessel, mold top, and uncured denture base material as shown in FIG. 3, but with the mold top forced downwardly on the mold vessel to apply compression to the uncured denture base material contained in the mold cavity.

Referring to FIGS. 1 and 3, and in the embodiment depicted therein, the mold vessel 110 is further comprised of a first compressible liner 122 that is contiguous with an inner surface 124 of the vessel bottom wall 120. The apparatus 100 is further comprised of a removable mold top 140 that is fittable to the top opening 102 of the mold vessel 110. The removable top 140 is comprised of a second compressible liner 142 contiguous with an inner surface 144 thereof. Referring to FIG. 1, FIG. 3, and FIG. 4, when the mold top 140 is fitted to the top opening 102 of the mold vessel 110 as indicated by arrows 149, a mold cavity 104 is formed within the inner surface 134 of the side wall 130 and between the first and second compressible liners 122, and 142.

Figure 2:
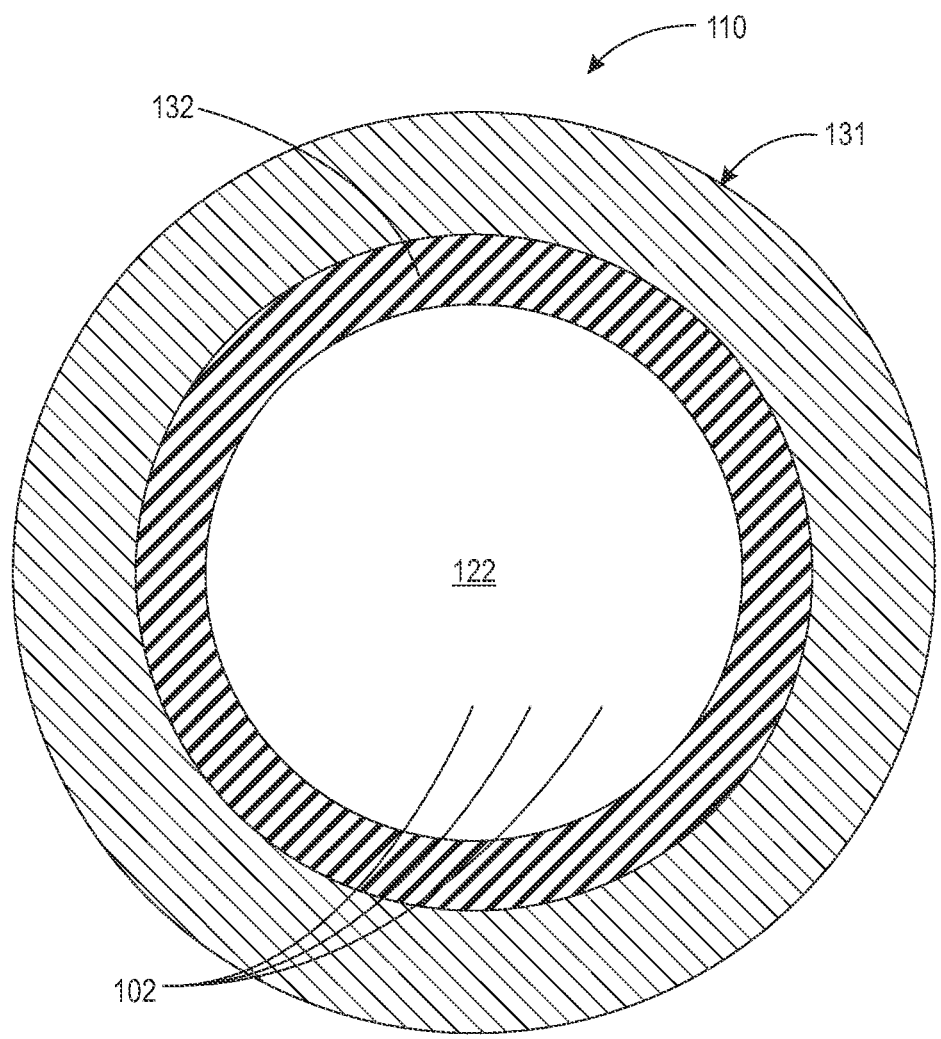
FIG. 2 is a top cross-sectional view of the mold vessel of FIG. 1A, taken along line FIG. 2-FIG. 2 of FIG. 1A.

Referring to FIGS. 1A and 2, an alternative embodiment of an apparatus 103 for molding a part is depicted. The side wall 131 of the mold vessel 110 is comprised of a third compressible liner 132 that is contiguous with the inner surface 134 of the vessel side wall 131.

The vessel bottom wall 120 and side wall 130, and the mold top 140 are made of suitable materials that have adequate structural strength for applying and containing pressure that is applied to the denture base material during its curing in the mold cavity 104. The vessel bottom wall 120 and/or vessel side wall 130 are also preferably made of a highly thermally conductive material, so as to conduct heat into the mold cavity 104 and facilitate curing of the denture base material when a heater is provided as part of the apparatus 100 or 103. In general, various metals such as steel or aluminum are suitable vessel wall and mold top materials.

The first, second, and optional third compressible liners 122, 142, and 132 are made of a suitable compressible elastomeric material such as silicone or a rubber material. The compressible liners 122, 132, and 142 are also preferably of a material that is resistant to degradation by heat so that they are suitable for use when a heater is provided as part of the apparatus 100. In general, the compressible liners 122, 132, and 142 are provided with a thickness and durometer so as to be compressible, and to become compressed when the mold cavity 104 is filled with uncured denture base material and pressurized. The silicone or rubber elastomeric material of the compressible liners 122, 132, and 142 may also be formed with at least some amount of closed-cell foam content so as to provide adequate compressibility and resiliency to cycle between compressed and uncompressed states during the part forming process.

A method of molding of a denture base disc with the apparatus 100 will now be described with reference in particular to FIGS. 3-6. As noted previously, the apparatus may be configured to mold parts other that a denture base disc, using moldable materials and operating conditions other than the exemplary ones described herein.

Prior to beginning the molding process, a denture base material is prepared for delivery into the mold cavity 104 of the apparatus 100. In one exemplary embodiment, the denture base material may be prepared by mixing high-impact polymethylmethacrylate polymer powder (PMMA) (empirical formula $C_5H_8O_2$, CAS Number 9011-14-7) and PMMA liquid containing methylmethacrylate monomer (CAS Number: 80-62-6) in a controlled environment to produce uncured denture base material. In certain embodiments, the controlled environment may be ambient air at between 60° F. to 80° F. and a relative humidity between 50 and 70%. The ratio of powder to liquid may be between 5 to 1 and 2 to 1 by weight. In one embodiment, the ratio of powder to liquid may be 3 parts powder to 1 part liquid by weight.

Referring first to FIG. 3, the mold top 140 is removed from the mold vessel 110, and the mold cavity 104 of the vessel 110 is filled with uncured denture base material 20, such as the PMMA material described above. The mold cavity 104 is filled with sufficient denture base material for molding of the desired part. The uncured denture base material is formulated as a semi-solid paste, such that a portion 22 of denture base material 20 may extend above the upper edge 136 of the side wall 130. The additional portion 22 is delivered because the elastomeric liners will be compressed to a lesser volume when the vessel is closed and pressure is applied to the denture base material 20, and also because during the curing process, the denture base material 20 will shrink to a smaller volume, as will be described subsequently herein.

After filling the mold vessel 110 with uncured denture base material 20, the vessel 110 may be subjected to vibration by a suitable vibration energy source (not shown). The vibration facilitates more rapid floating of any bubbles of air contained in the uncured denture base material 20 to the surface thereof, and their subsequent rupture.

Referring to FIG. 4, the removable mold top 140 is fitted to the mold vessel 110. A force is applied to the mold top 140 as indicated by arrow 148 by suitable means such as a press (not shown), so as to contact the mold top 140 with the upper surface 136 of the side wall 130, thereby enclosing the mold cavity 104, and applying pressure to the uncured denture base material 20 contained therein. It can be seen that the first and second compressible liners 122 and 142 of the bottom wall 120 and mold top 140 have gone from an uncompressed state as shown in FIG. 3 to the respective compressed states 122C and 142C shown in FIG. 4. Additionally, the uncured denture base material 20 has deformed and flowed in the mold cavity 104 so as to completely fill the mold cavity 104 and contact the compressed compressible liners 122C and 142C.

Figure 5:
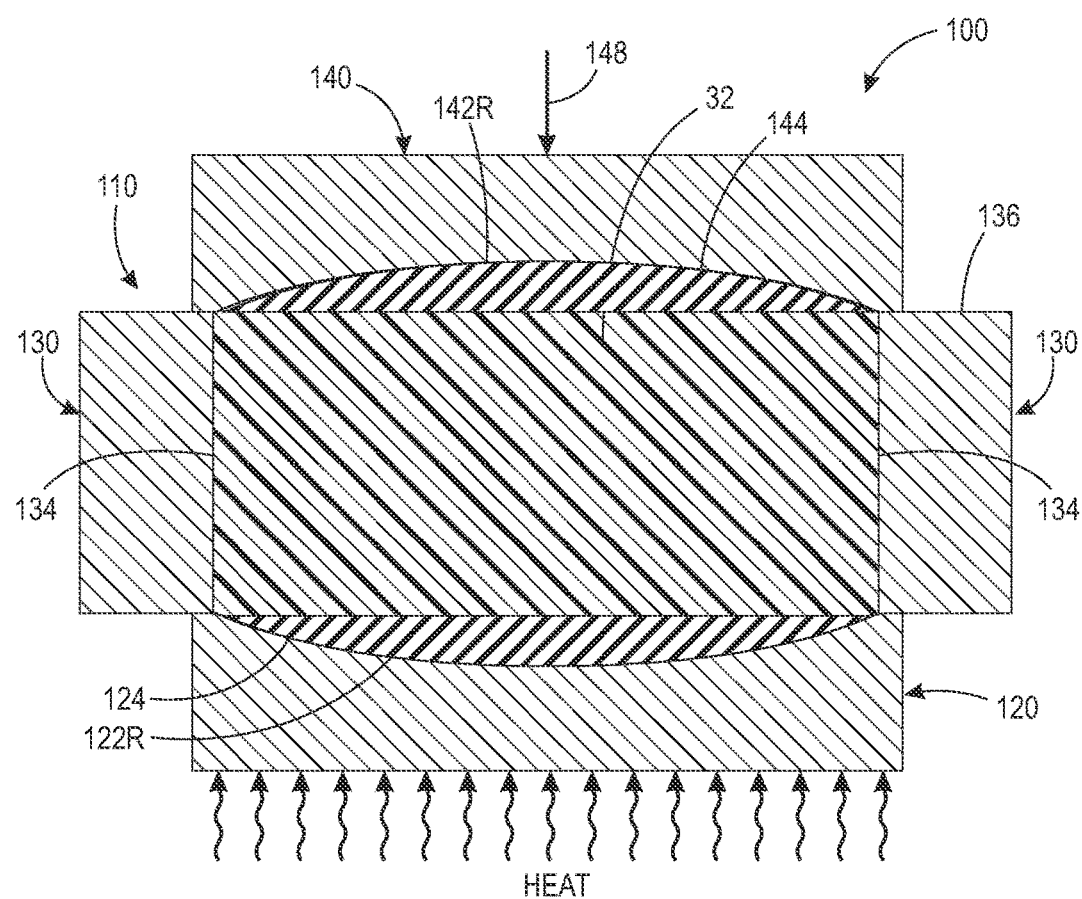
FIG. 5 is a schematic side cross-sectional view of the mold vessel and mold top of FIGS. 1, 3, and 4 with cured denture base material contained in the mold cavity after polymerization/curing of the material.
Figure 6:
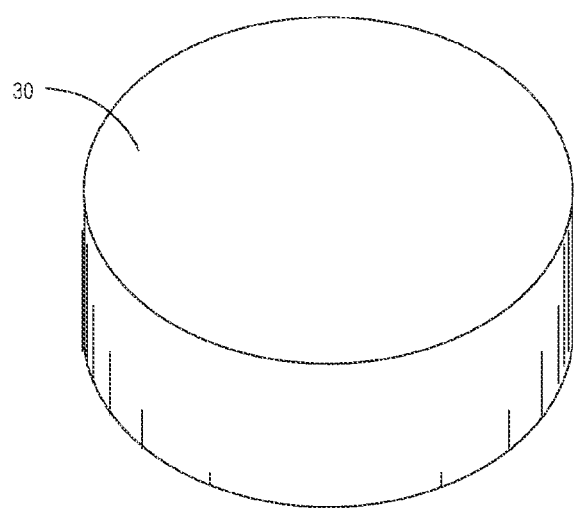
FIG. 6 is a perspective view of a disc of cured denture base material after removal from the mold vessel.
Figure 11:
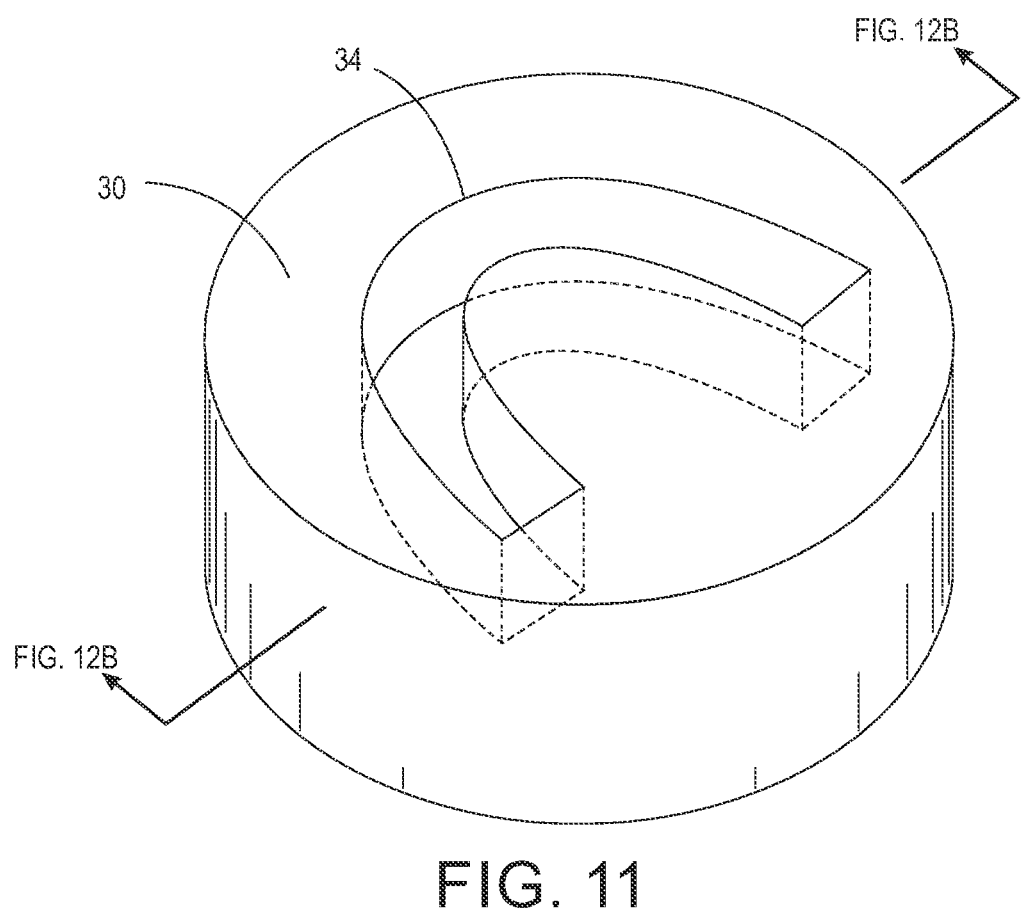
FIG. 11 is a perspective view of the disc of FIG. 6 with a U-shaped trough cut into the disc for subsequent denture fabrication steps.
Figure 12A:
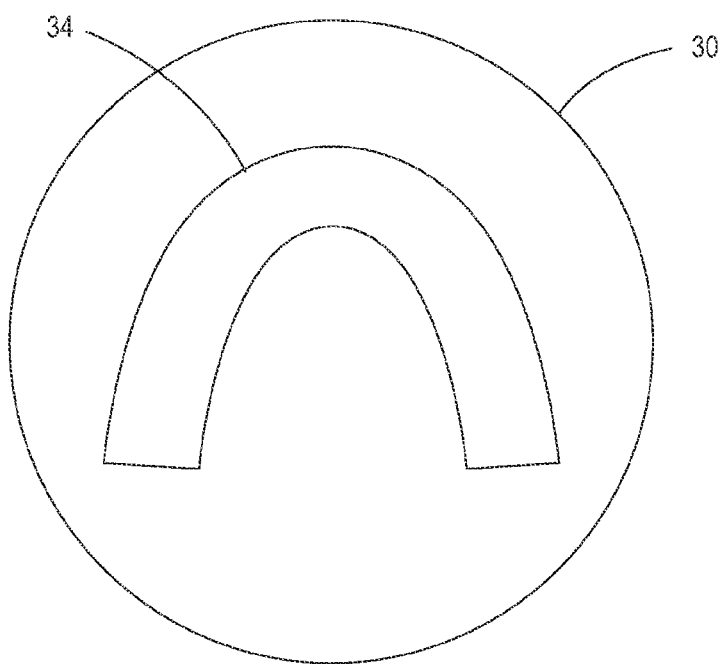
FIG. 12A is a top view of the U-shaped trough of the disc of FIG. 11.
Figure 12B:
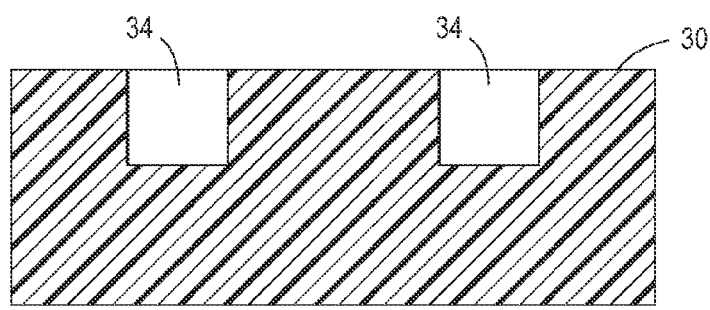
FIG. 12B is a side cross-sectional view of the U-shaped trough of the disc of FIG. 11, taken along line FIG. 12B-FIG. 12B thereof.
Figure 13:
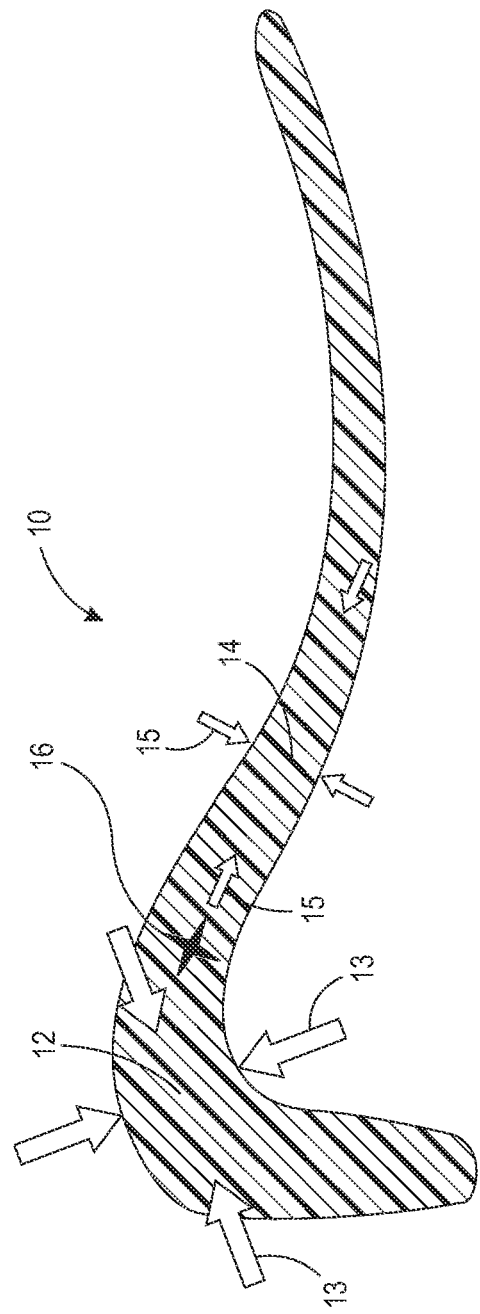
FIG. 13 is a cross-sectional view of a denture made according to prior art methods, with internal stresses that result from the prior art methods.

Referring to FIG. 5, the uncured denture base material has been cured to an at least partially cured and solid state 32. It can be seen that the during this curing, the at least partially cured solid state denture base material 32 shrinks to a lesser volume than the uncured denture base material 20 of FIG. 4. Concurrently, the first and second compressible liners expand from respective compressed states 122C and 142C to less compressed or relaxed states 122R and 142R. The compressible liner materials and volumes are chosen such that the expansion in compressible liner volume, i.e., the difference between the volumes of the compressed liners 122C and 142C and relaxed liners 122R and 142R is substantially equal to the volume of shrinkage of denture base material during the at least partial curing. (As used in this instance, "substantially" means that the expansion in compressible liner volume is sufficiently close to the volume of shrinkage of denture base material during the at least partial curing so as to result in the finished denture disc 30 being cylindrical as shown in FIG. 6, such that subsequent denture prostheses fabrication can then proceed as shown in FIGS. 11-12B and described subsequently herein.) In that manner, the volume of the mold cavity 104 is made variable by varying the volume of the compressible liners 122 and 142. For certain denture base materials, the amount of shrinkage is typically between about 5 and about 8 volume percent.

Figure 5A:
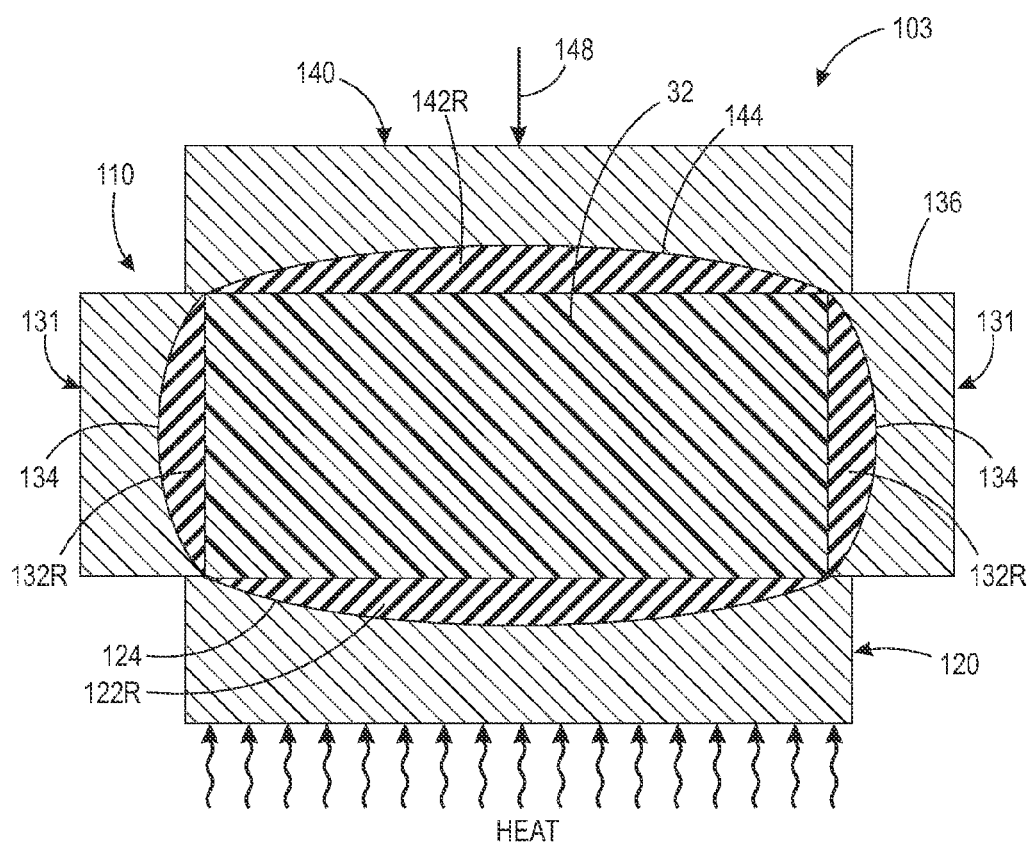
FIG. 5A is a schematic side cross-sectional view of the alternative mold vessel and mold top of FIG. 1A with cured denture base material contained in the mold cavity after polymerization/curing of the material.

FIG. 5A depicts the part molding apparatus 103 of FIG. 1A, but with cured solid state denture base material 32 contained therein. It can be seen that the third elastomeric liner 132 has been in contact with the denture base material during the filling, molding, and curing steps and is in a relaxed state 132R.

Advantageously, the mold vessel 110 and mold top 140, and the elastomeric liners contained therein work cooperatively to cause the denture base disc to cure in a homogenous manner with consistent pressure on all sides so that residual stresses in the finished disc 30 are minimized. In certain embodiments, the materials and dimensions of the mold vessel 110 and mold top 140, and the elastomeric liners contained therein are chosen so as to provide between 4000 and 8000 pounds per square inch of pressure during the molding and curing steps. A press (not shown) may be provided to compress the mold top 140 onto the mold vessel 110 to provide this pressure. In certain embodiments, this pressure may be maintained for a period of two hours.

The partially cured denture base material 32 may be "aged" in the mold cavity 104, until the polymerization of the denture base material is complete to form a solid denture base disc 30. The removable mold top 140 may then be removed from the mold vessel 110, and the solid denture base disc 30 may be removed from the mold vessel 110 as shown in FIG. 6. In certain embodiments, the denture base disc 30 may be about 100 millimeters in diameter, and about 20 to 40 millimeters thick.

The apparatus 100 may be provided with a heat source for heating the mold vessel 110, and the partially cured denture base material 32 contained therein, so as to facilitate the completion of polymerization to form the solid denture base disc 30. In certain embodiments, the heat source may optionally be provided such that the mold vessel 110 is heated at only one location or region. It can be seen that in the embodiments depicted in FIGS. 5 and 5A, the bottom wall 120 of the mold vessel 110 is heated. A heater (not shown) may be provided in thermal communication with the bottom wall 120 of the mold vessel 110, thereby heating the bottom wall 120 and the partially cured denture base material 32 contained in the mold vessel 110.

In certain embodiments, the curing of the denture base material may optionally be performed in a sequence of steps at different temperatures and durations. After a first heating step is complete, the denture disc may be "aged," either within the mold vessel 110, or after removal from the vessel 110 as shown in FIG. 6, in order to reduce the content of residual monomer, which reduces internal stresses in the solid disc 30. In one embodiment, the mold vessel 110 containing the denture base material may be removed from the aforementioned press, then placed in a small stationary press and heated to 185° F. for 8 hours, and then immersed in boiling water for 20 minutes to produce the solid disc 30.

In another embodiment, the at least partially cured denture base material 20 may be aged at a first increased temperature to produce cured denture base material. The cured denture base material may then be heated to a second increased temperature over a period of at least 0.5 hours, and maintained at the second increased temperature for at least 0.5 hours. The first temperature may be between 140 and 200° F., and the second temperature may be between 200° F. and 212° F.

In another embodiment, the aging may be performed for 10 days at 165° F. As a final curing step, the denture disc 30 may be very slowly heated (i.e. a heating time of between 0.5 hours and 3 hours) to 250° F. and held at that temperature for at least about 30 minutes, and preferably about 2 hours to remove essentially all residual monomer and to complete de-stressing of the solid polymer of the denture base disc 30. The heat is then very gradually reduced, allowing the cured denture disc to return to room temperature slowly to avoid creating internal stress. The heat may be reduced over a period of about 2 hours.

The method may include steps of increasing the pressure applied to the uncured denture base material 20 in the mold cavity 104 during the curing process. To accomplish such steps, the apparatus is provided with means for increasing the pressure applied to the uncured denture base material 20 in the mold cavity 104. The means for increasing the pressure is also referred to herein as a "pressure intensifier." The pressure intensifier is useful for curing denture base materials that undergo a higher amount of shrinkage during curing, as it further compresses the uncured denture base material 20 in the mold cavity 104 prior to curing.

In certain embodiments, the pressure intensifier may be comprised of an aperture in the mold vessel 110, which contains the uncured denture base material 20 as a result of closing the vessel 110 by fitting the mold top 140 onto the mold vessel 110. Pressure on the uncured denture base material 20 is applied via the aperture by hydraulic means or mechanical means such as a piston, thereby forcing uncured denture base material 20 from the aperture into the vessel 110 and pressurizing the material 20. As a result of the increased applied pressure provided by the pressure intensifier, the bottom wall compressible liner 122 and/or side wall compressible liner 132 and the mold top compressible liner 142 are further compressed.

FIGS. 7-10 depict one embodiment of a pressure intensifier. It is to be understood that the embodiment in FIGS. 7-10 is to be considered as exemplary, and that other apparatus for intensifying the pressure of the denture base material 20 in the mold cavity 104 are contemplated. Additionally, it is noted that the apparatus 101 depicted in FIGS. 7-10 is comprised of a mold vessel 110 having a side wall 131 that includes a third elastomeric liner 132, as depicted in FIGS. 1A and 5A and described previously. It is to be understood that the use of the third elastomeric liner 132 is optional, and that a pressure intensifier may be used with the apparatus 100 of FIG. 1 and FIGS. 3-5.

Figure 7:
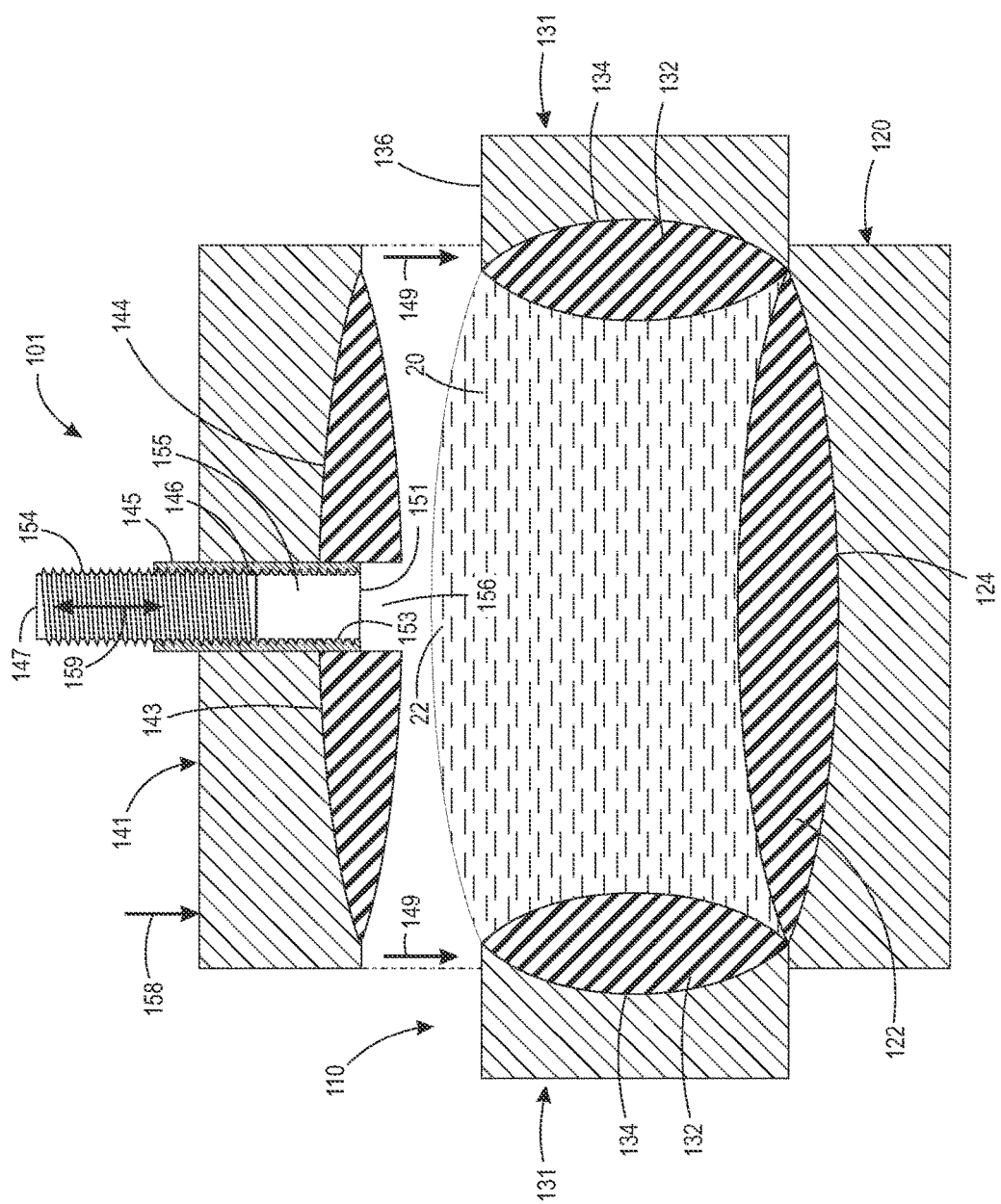
FIGS. 7-10 depict means for increasing the pressure applied to uncured denture base material disposed in the mold cavity prior to curing of the material, and the operation of such means, including the compression of compressible liners of the mold assembly.

Referring first to FIG. 7, an apparatus 101 for molding a part, such as a denture base disc, is comprised of a mold vessel 110 as described previously herein, and a removable mold top 141. The removable mold top 141 is similar to the mold top 140 shown in FIGS. 1-5 and described previously herein. However, mold top 141 differs from mold top 140 in that it is provided with a pressure port 146 and is further comprised of a pressure intensifier.

In the embodiment depicted in FIGS. 7-10, the pressure intensifier is comprised of a pipe 145 and a piston 147. The pipe 145 is disposed in the pressure port 146 and retained therein during the molding process. The pipe 145 may be retained by being in an interference fit with the pressure port 146, or the pipe 145 and pressure port 146 may be engaged with matching threads (not shown). Alternatively, the mold top 141 and pipe 145 may be of unitary construction machined from a single piece of material.

The pipe 145 extends inwardly beyond the inner surface 144 of the mold top 141, and has an inner end 151 that is approximately coplanar with the bottom surface 152 of the mold top 141. The piston 147 is movable axially between an outward position to an inward position in the internal bore of the pipe 145 as indicated by bidirectional arrow 159. In the embodiment depicted in FIGS. 7-10, the inner bore of pipe 145 is provided with threads 153, and the piston 147 is provided with corresponding threads 154, so that the piston 147 may be advanced and retracted axially within the pipe 145 by rotation of the piston 147. In an alternative embodiment (not shown), the piston 147 may be driven hydraulically or pneumatically within the inner bore of the pipe 145. Other means of driving the piston 147 within the pipe 145 are contemplated. In any case, the piston 147 is operable within the pipe 145 so as to apply pressure to uncured denture base material 20 within the mold cavity 104 during the molding process as will be described subsequently. Additionally, the lower end of the piston and the lower portion of the inner bore of the pipe 145 define a pipe cavity volume 155, which receives uncured denture base material 20 through a port 156 in the mold top compressible liner 141 during the initial step of the molding process, as will also be described subsequently.

In the method of molding a denture base disc or other part within the assembly 101, the mold cavity of the vessel 110 is filled with uncured denture base material 20, such as the PMMA. The mold cavity 104 may be filled with an excess 22 of uncured denture base material, i.e., a volume greater than the mold cavity 104, as described previously with reference to FIG. 3, extending above the upper edge 136 of the side wall 131.

Figure 8:
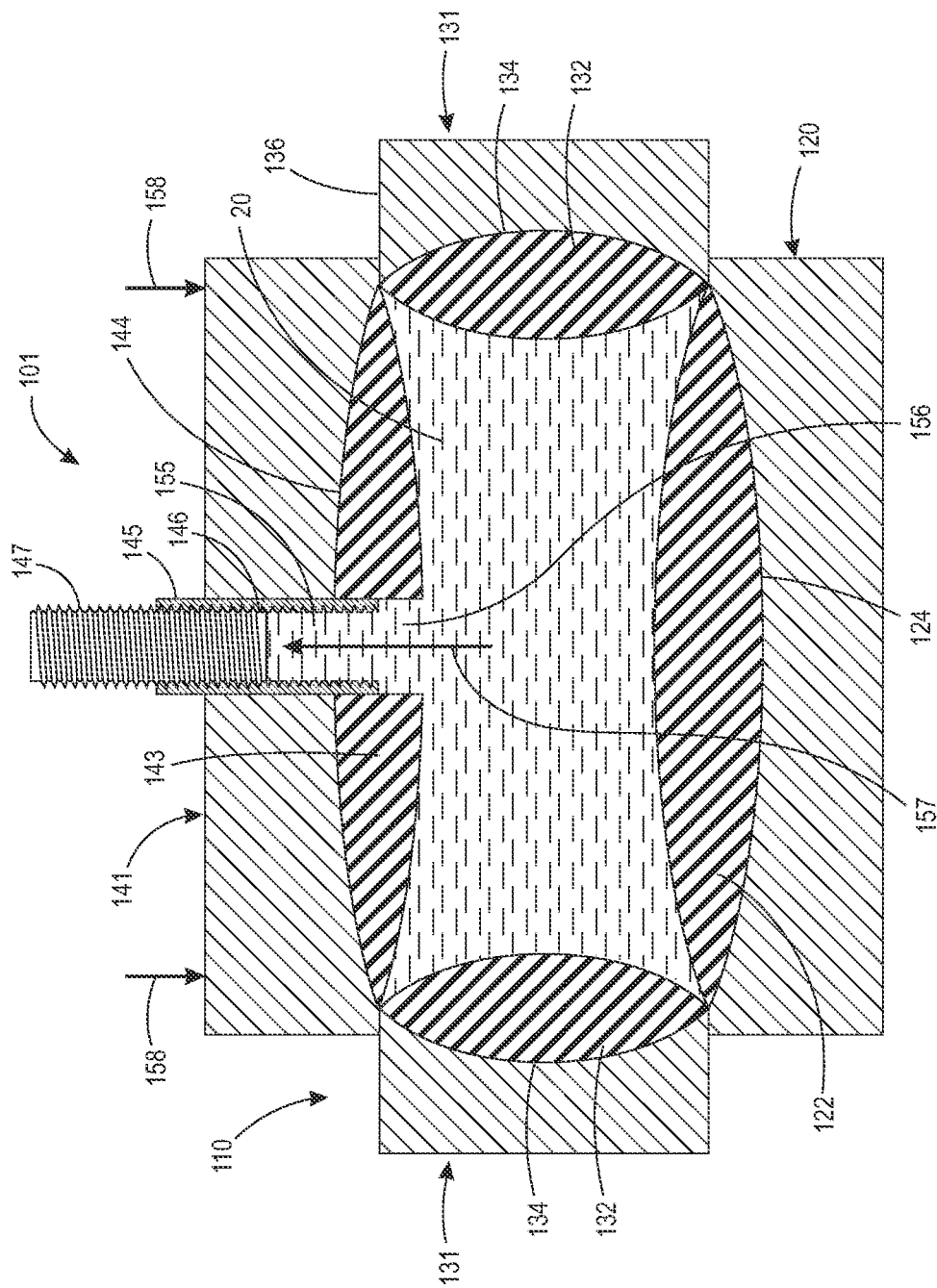

Referring to FIG. 8, the removable mold top 141 is fitted to the mold vessel 110. A force is applied to the mold top 141 as indicated by arrows 158 by suitable means such as a press (not shown), so as to contact the mold top 141 with the upper surface 136 of the side wall 131, thereby enclosing the mold cavity 104, and applying initial pressure to the uncured denture base material 20 contained therein. However, in contrast to the mold apparatus 100 of FIG. 4 and described previously, it can be seen that the first, second, and third compressible liners 122, 143, and 132 of the bottom wall 120, side wall 131, and mold top 141 have not gone from the uncompressed state shown in FIG. 7 to a compressed state. Instead, the uncured denture base material 20 has been caused to flow under the initial pressure upwardly into the port 156 of the mold top compressible liner 141 and the pipe cavity volume 155 within the pipe 145 as indicated by arrow 157.

Figure 9:
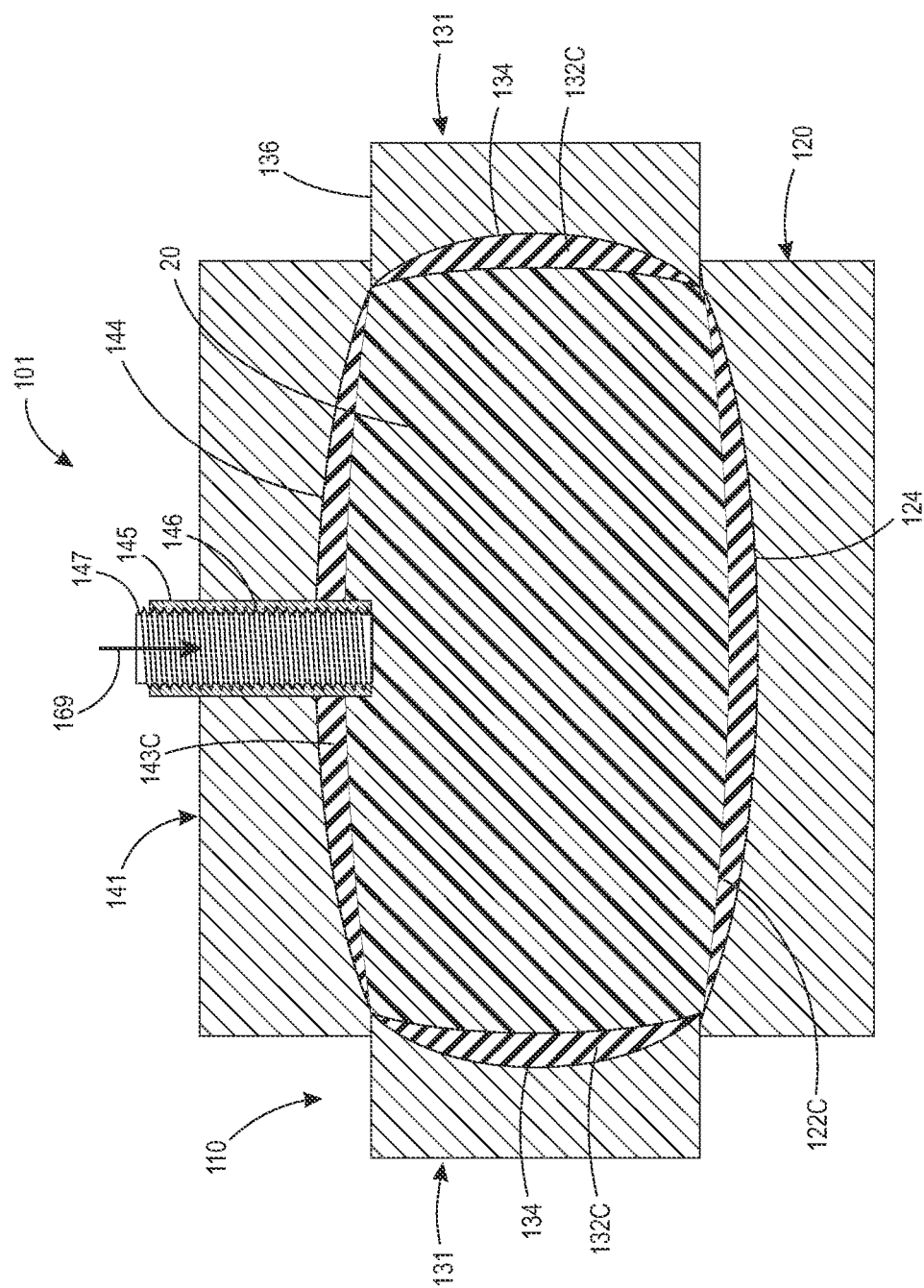

Referring to FIGS. 8 and 9, the pressure upon the uncured denture base material 20 is then increased by driving the piston 147 of the pressure intensifier inwardly as indicated by arrow 169 from the outward position shown in FIG. 8 within the bore of the pipe 145 to the inward position shown in FIG. 9. The volume of uncured denture base material that was previously contained with the pipe cavity volume 155 of the pipe 145 is displaced into the mold cavity 104 of the mold vessel 110. This displacement increases the pressure of the denture base material 20 within the mold cavity, and causes compression of the first, second, and third compressible liners 122, 143, and 132 into compressed states 122C, 143C, and 132C.

Figure 10:
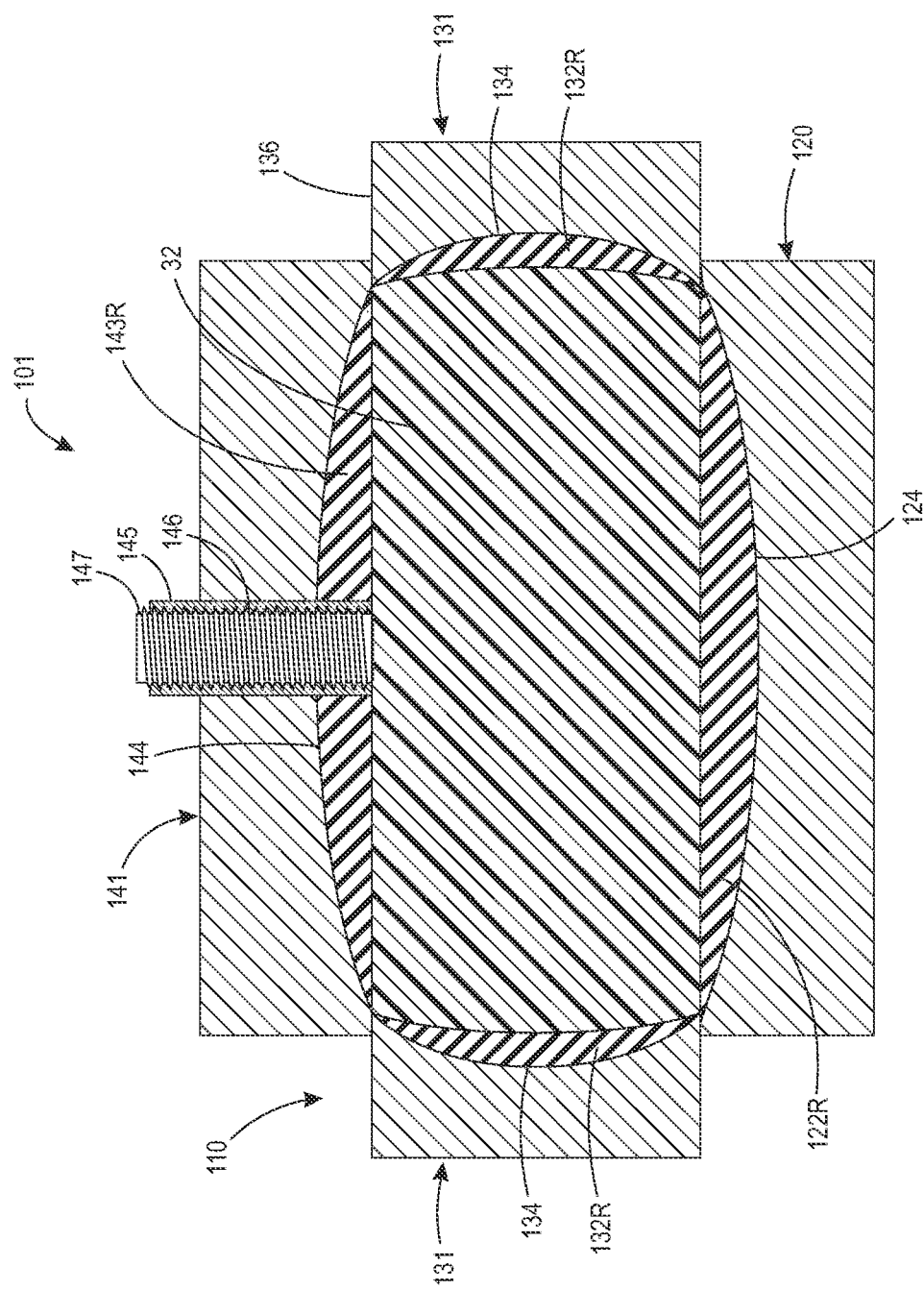

Referring to FIG. 10, the denture base material 20 is then cured into solid denture base material 32. It can be seen that the during this curing, the solid denture base material 32 shrinks to a lesser volume than the uncured denture base material 20 of FIGS. 8 and 9. Concurrently, the first, second, and third compressible liners expand from respective compressed states 122C, 143C, and 132C to less compressed or relaxed states 122R, 143R, and 132R.

It is to be understood that although the pressure intensifier is shown as being a part of the mold top 141 in FIGS. 7-10, other configurations of the apparatus 101 are contemplated. The pressure intensifier may be provided in the bottom wall 120 or the side wall 131 of the apparatus 101.

The curing process may be facilitated by the application of heat to the mold vessel 110 as described previously. The denture base disc may undergo an aging process at a series of times and temperatures as described previously. When at least the initial curing process is complete, the solid denture base disc 30 may be removed from the molding apparatus 101 as shown in FIG. 6.

After the denture base disc 30 is made according to the methods described herein, a denture may be fabricated according to the methods disclosed in the aforementioned U.S. Provisional Patent Application No. 61/782,888, U.S. patent application Ser. No. 14/180,260, and U.S. Pat. No. 8,641,938. Referring to FIGS. 11, 12A, and 12B, the denture fabrication process continues with the forming of a U-shaped cavity 34 in the denture base disc 30. The U-shaped cavity 34 is formed to match the contour of natural teeth as arranged on maxillae or on a mandible. The denture fabrication process proceeds as described in the above aforementioned U.S. patent applications and patent.

It is, therefore, apparent that there has been provided, in accordance with the present invention, a method and apparatus for making a denture base disc or other part that has minimal internal stresses. Having thus described the basic concept of the invention, it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

We claim:
1. A method of fabricating a denture base disc, the method comprising:
   a) filling a mold cavity formed within a mold vessel with an uncured denture base material, the mold cavity bounded by a first compressible liner having a first uncompressed volume and contiguous with a bottom wall of the vessel;
   b) contacting a second compressible liner of a removable mold top with a top surface of the uncured denture base material, the second compressible liner contiguous with an inner surface of the removable mold top and having a second uncompressed volume;
   c) forcing the removable mold top to contact an upper surface of the mold vessel and enclose the mold cavity, and cause pressurization of the uncured denture base material by deforming the first compressible liner from the first uncompressed volume to a first compressed volume and deforming the second compressible liner from the second uncompressed volume to a second compressed volume; and
   d) curing the uncured denture base material into an at least partially cured and solid state, wherein the at least partially cured solid state denture base material shrinks to a lesser volume than the uncured denture base material, and wherein the first compressible liner expands to a first relaxed volume and the second compressible liners expands to a second relaxed volume.

2. The method of claim 1, further comprising applying increased pressure to the uncured denture base material prior to curing, thereby increasing the amount of deforming of the first and second compressible liners to the respective first and second compressed volumes.

3. The method of claim 2, wherein the applying increased pressure to the uncured denture base material is performed using a pressure intensifier in communication with the uncured denture base material in the cavity of the mold vessel.

4. The method of claim 3, wherein the pressure intensifier is comprised of a piston operable within a pipe, and the applying increased pressure to the uncured denture base material is comprised of displacing the piston within the pipe inwardly, thereby displacing uncured denture base material from a cavity within the pipe into the cavity of the mold vessel.

5. The method of claim 1, further comprising aging the at least partially cured solid state material at a first increased temperature to produce cured denture base material.

6. The method of claim 5, further comprising heating the cured denture base material to a second increased temperature over a period of at least 0.5 hours, and maintaining the cured denture base material at the second increased temperature for at least 0.5 hours.

7. The method of claim 1, wherein when curing the uncured denture base material into an at least partially cured and solid state, the volume of shrinkage of denture base material is substantially equal to the sum of the change in volume of the first compressible liner from the first compressed volume to the first relaxed volume plus the change in volume of the second compressible liner from the second compressed volume to the second relaxed volume.

8. The method of claim 1, wherein the mold cavity is further bounded by a third compressible liner having a third uncompressed volume and contiguous with a side wall of the vessel, and wherein the forcing the removable mold top to contact an upper surface of the mold vessel deforms the third compressible liner from the third uncompressed volume to a third compressed volume, and wherein during curing the uncured denture base material into an at least partially cured and solid state, the third compressible liner expands to a third relaxed volume.

9. The method of claim 8, wherein when curing the uncured denture base material into an at least partially cured and solid state, the volume of shrinkage of denture base material is substantially equal to the sum of the change in volume of the first compressible liner from the first compressed volume to the first relaxed volume plus the change in volume of the second compressible liner from the second compressed volume to the second relaxed volume plus the change in volume of the third compressible liner from the third compressed volume to the third relaxed volume.

10. The method of claim 1, further comprising removing the at least partially cured and solid state denture base material from the mold cavity.

11. The method of claim 10, wherein the removed solid state denture base material is cylindrical in shape.

12. The method of claim 1, wherein the first and second compressible liners are formed from a compressible elastomer.

13. The method of claim 12, wherein the first and second compressible liners are formed from silicone elastomer.

14. The method of claim 12, wherein the first and second compressible liners are formed from a closed cell foam of the elastomer.

15. The method of claim 1, wherein the uncured denture base material is comprised of a mixture of polymethylmethacrylate polymer powder polymethylmethacrylate liquid including methylmethacrylate monomer.

16. The method of claim 1, wherein the at least partially cured denture base material is comprised of polymethylmethacrylate polymer.

17. The method of claim 1, further comprising curing the at least partially cured solid state denture base material to a fully cured denture base material.

18. The method of claim 17, wherein the curing the at least partially cured solid state denture base material to a fully cured denture base material includes relieving internal stresses in the at least partially cured solid state denture base material.

* * * * *